(12) United States Patent
Mest et al.

(10) Patent No.: US 6,405,067 B1
(45) Date of Patent: Jun. 11, 2002

(54) CATHETER WITH TIP ELECTRODE HAVING A RECESSED RING ELECTRODE MOUNTED THEREON

(75) Inventors: Robert A. Mest, Long Beach, CA (US); Hiroshi Nakagawa, Edmond, OK (US)

(73) Assignee: Biosense Webster, Inc., Diamond Bar, CA (US)

( * ) Notice: Subject to any disclaimer, the term of this patent is extended or adjusted under 35 U.S.C. 154(b) by 158 days.

(21) Appl. No.: 09/611,849

(22) Filed: Jul. 7, 2000

(51) Int. Cl.$^7$ ................................................. A61B 5/04
(52) U.S. Cl. ........................ 600/374; 606/41; 607/101; 607/122
(58) Field of Search ............................... 600/373, 374, 600/381; 607/119, 120, 122, 96, 99, 101, 102, 104, 105, 113, 116; 606/41, 46, 49

(56) References Cited

U.S. PATENT DOCUMENTS

| | | | |
|---|---|---|---|
| 4,444,195 A | 4/1984 | Gold | 128/642 |
| 4,481,953 A | 11/1984 | Gold et al. | 128/786 |
| 4,966,597 A | 10/1990 | Cosman | 606/50 |
| 5,085,659 A | 2/1992 | Rydell | 606/47 |
| 5,179,952 A | 1/1993 | Buinevicius et al. | 128/642 |
| 5,230,349 A | 7/1993 | Langberg | 128/786 |
| 5,315,996 A | 5/1994 | Lundquist | 128/642 |
| 5,383,922 A * | 1/1995 | Zipes et al. | 607/122 |
| 5,398,683 A * | 3/1995 | Edwards et al. | 607/116 |
| 5,462,544 A | 10/1995 | Saksena et al. | 606/15 |
| 5,520,684 A | 5/1996 | Imran | 606/41 |
| 5,749,914 A | 5/1998 | Janssen | 607/116 |
| 5,782,760 A | 7/1998 | Schaer | 600/381 |
| 5,810,802 A | 9/1998 | Panescu et al. | 606/31 |
| 5,891,027 A | 4/1999 | Tu et al. | 600/374 |
| 5,919,222 A | 7/1999 | Hjelle et al. | 607/122 |
| 5,967,976 A | 10/1999 | Larsen et al. | 600/374 |
| 5,971,980 A | 10/1999 | Sherman | 606/34 |
| 6,001,095 A * | 12/1999 | De la Rama et al. | 6/41 |
| 6,024,739 A * | 2/2000 | Ponzi et al. | 600/374 |

* cited by examiner

*Primary Examiner*—Linda C. M. Dvorak
*Assistant Examiner*—David M. Ruddy
(74) *Attorney, Agent, or Firm*—Christie, Parker & Hale, LLP

(57) ABSTRACT

A catheter particularly suitable for bipolar mapping and ablating comprises an elongated flexible body having a distal region and at least one lumen extending therethrough. A tip electrode is mounted on the distal region. The tip electrode has an exposed distal region having an outer diameter, a recessed central region having an outer surface proximal to the exposed distal region, and a proximal region having an outer diameter and an outer surface proximal to the central region. The recessed central region has an outer diameter less than the outer diameters of the exposed distal region and the proximal region. The central region and the proximal region are provided with an electrically insulating and thermally conductive layer over at least a portion of their outer surfaces. A ring electrode is mounted on the recessed central region. The ring electrode has an outer diameter less than the outer diameters of the exposed distal region and the proximal region. With this design, the exposed region of the tip electrode is in direct contact with the heart tissue, and thus senses both the local activation energy (near-field signals) at the point of contact with the heart tissue and far field activation energy (far-field signals) received by the exposed region through the blood. However, the recessed electrode is protected from direct contact with the heart tissue, but does contact with surrounding blood. The close proximity of the recessed electrode to the exposed region enables the recessed electrode to receive approximately the same far-field signals as the exposed region. However, the recessed electrode does not pick up the local activation potential (near-field signals) that are received by the exposed region. This design permits the creation of high resolution electrograms.

25 Claims, 6 Drawing Sheets

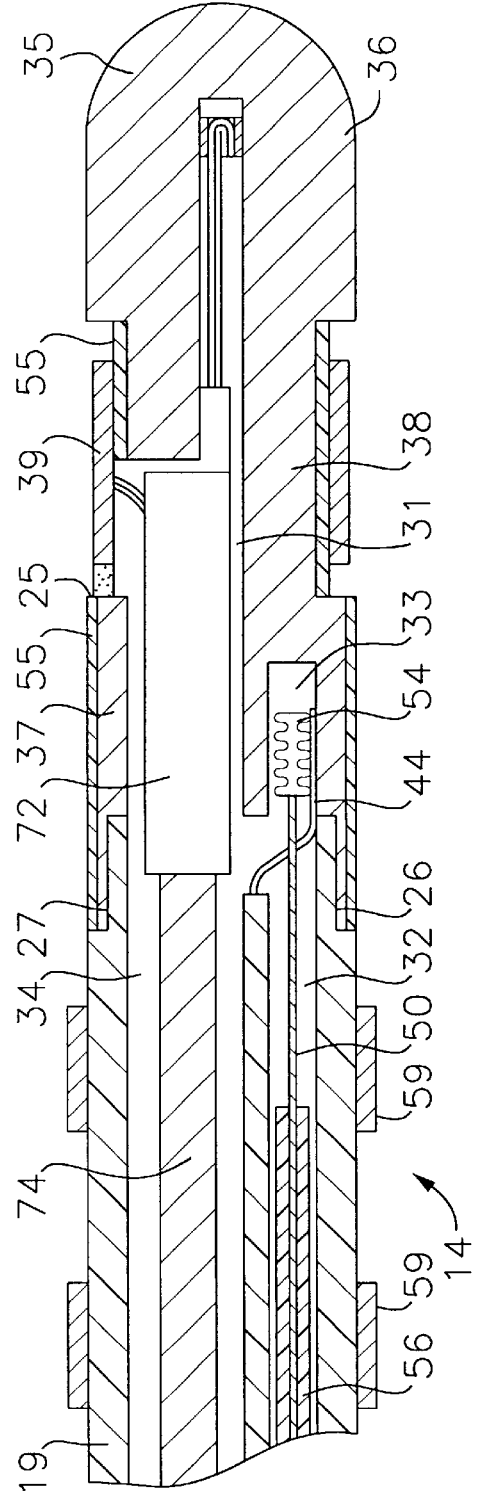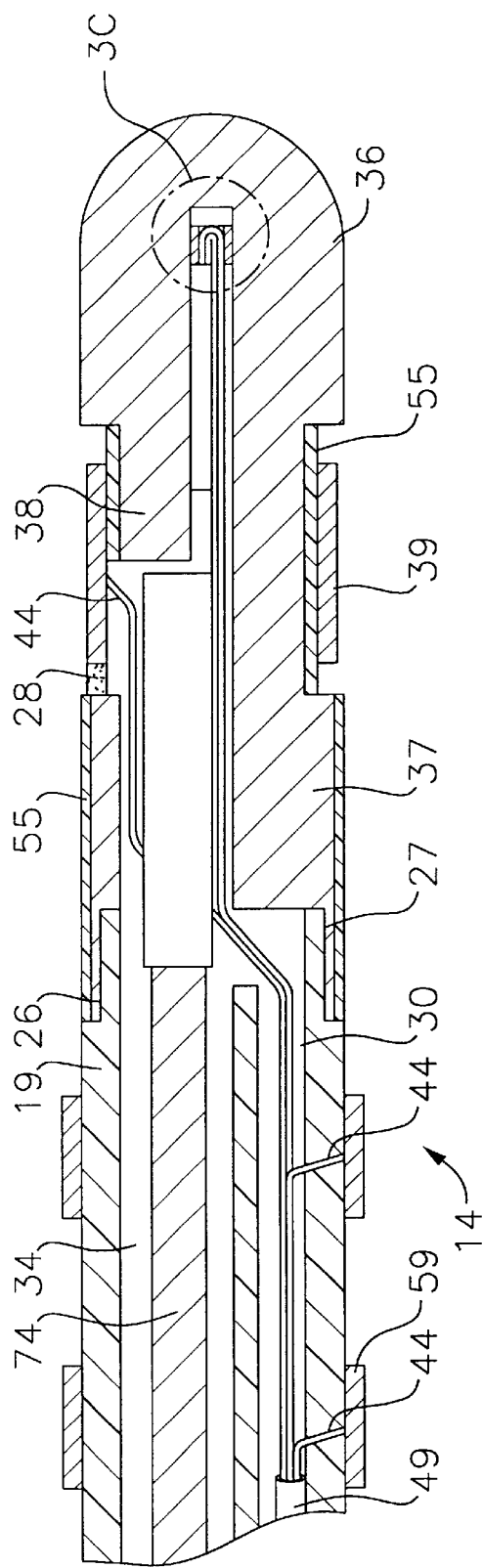

CATHETER WITH TIP ELECTRODE HAVING A RECESSED RING ELECTRODE MOUNTED THEREON

FIELD OF THE INVENTION

The present invention is directed to a catheter for diagnosis and treatment of the heart, and more particularly to a catheter comprising a tip electrode having a recessed ring electrode mounted thereon.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Once the catheter is positioned within the heart, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with or in close proximity to the endocardium. By monitoring the electrical signals at the endocardium, aberrant conductive tissue sites responsible for the arrhythmia can be pinpointed.

For mapping, it is desirable to have a relatively small mapping electrode. It has been found that smaller electrodes record more accurate and discrete electrograms. Additionally, if a bipolar mapping arrangement is used, it is desirable that the two electrodes of the mapping arrangement be in close proximity to each other and that they be similar in size to produce more accurate and useful electrograms.

Additionally, it has been found that standard bipolar mapping catheters have limited accuracy because both electrodes pick up near field electrical signals emanating from the conductive endocardial tissues due to their contact with the heart tissue, and far-field electrical signals that propagate from other regions of the heart due to their contact with the blood. The far-field signals interfere with the near-field signals, making accurate measurement of the near-field signals difficult.

Once the origination point for the arrhythmia has been located in the tissue, the physician uses an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

A typical ablation procedure involves providing a reference electrode, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, a thin transparent coating of dehydrated blood protein can form on the surface of the electrode. If the temperature continues to rise, this dehydrated layer can become progressively thicker, resulting in char and/or thrombus on the electrode surface. The creation of char and thrombus is unsafe, as the char and thrombus can be dislodged from the electrode during the procedure or during removal of the catheter after the procedure.

In clinical practice, it is desirable to reduce or eliminate the formation of char and thrombus and, for certain cardiac arrhythmias, to create larger and/or deeper lesions. One method for accomplishing this end is to monitor the temperature of the ablation electrode and to control the RF current delivered to the ablation electrode based on this temperature. If the temperature rises above a preselected value, the current is reduced until the temperature drops below this value.

Another method for determining whether char and thrombus is forming is by monitoring the impedance. Specifically, because dehydrated biological material has a higher electrical resistance than endocardial tissue, impedance to the flow of electrical energy into the tissue also increases. A significant impedance rise thus indicates the formation of char and/or thrombus. With a relatively large electrode, e.g., an 8 mm electrode, an impedance rise from char and thrombus formation may not be easily detected because the char and thrombus is formed over a relatively small percentage of the total surface area of the electrode. In contrast, if the electrically active surface area of the electrode is relatively small, char and thrombus will form over a relatively larger area of the electrode, making detection by impedance measurements easier.

The cooling effect of the blood on the electrode is dependent on the thermal properties of the ablation electrode, and in particular its surface area. Typically ablation electrodes are relatively long, most commonly at least about 4 mm and up to about 8 mm, to provide sufficient surface area for cooling. However, such electrodes are less suitable for mapping because, as discussed above, more accurate electrograms can be obtained with a smaller mapping electrode. It is desirable for electrophysiologists use the same catheter for mapping and ablation during a single procedure because, once a site is identified with a high resolution mapping electrode catheter as a target for therapy, it would be difficult to locate that site again with another catheter, particularly where the other catheter has a larger tip electrode. Accordingly, a need exists for an electrode catheter that has a relatively small surface area for enhanced mapping, but has good thermal properties for enhanced cooling during ablation.

Another disadvantage of typical ablation electrodes is that it is sometimes difficult to accurately predict lesion size because the lesion size can vary depending on the orientation of the ablation electrode. For example, typically a 7 French catheter (having an outer diameter of just over 2 mm) is provided with an ablation tip electrode at its distal end having a length ranging from about 4 mm to about 8 mm. If the ablation electrode is provided in perpendicular relation to the tissue, a relatively small surface area of the electrode is in contact with the tissue. In contrast, a relatively larger surface area would be in contact with the tissue if the ablation electrode were in a generally parallel relationship to the tissue, i.e., if the ablation electrode were positioned on its side. It is often difficult for the physician to determine the precise orientation of the tip electrode relative to the tissue because the tissue is not visible with fluoroscopy. The size of the lesion is often related to the amount surface area in contact with the tissue. As a result, there is less predictability in lesion size.

Thus, although it is desirable to have a relatively long electrode for cooling purposes, it is desirable to have a relatively small electrically active surface area for obtaining more discrete electrograms, for more accurately detecting char and thrombus formation, and for enhancing the predictability of lesion size, as well as to have a bipolar electrode arrangement that more accurately measures near-field activity.

SUMMARY OF THE INVENTION

The present invention is directed to a catheter that is particularly suitable for bipolar mapping and ablation. In one embodiment, the catheter comprises an elongated flexible body having a distal region and at least one lumen extending therethrough. A tip electrode is mounted on the distal region. The tip electrode has an exposed distal region having an outer diameter, a recessed central region having an outer surface proximal to the exposed distal region, and a proximal region having an outer diameter and an outer surface proximal to the central region. The recessed central region has an outer diameter less than the outer diameters of the exposed distal region and the proximal region. The central region and the proximal region are provided with an electrically insulating and thermally conductive layer over at least a portion of their outer surfaces. A ring electrode is mounted on the recessed central region. The ring electrode has an outer diameter less than the outer diameters of the exposed distal region and the proximal region.

With this design, the exposed region of the tip electrode is in direct contact with the heart tissue, and thus senses both the local activation energy (near-field signals) at the point of contact with the heart tissue and far field activation energy (far-field signals) received by the exposed region through the blood. However, the recessed electrode is protected from direct contact with the heart tissue, but does contact with surrounding blood. The close proximity of the recessed electrode to the exposed region enables the recessed electrode to receive approximately the same far-field signals as the exposed region. However, the recessed electrode does not pick up the local activation potential (near-field signals) that are received by the exposed region. Thus, this design permits the creation of high resolution electrograms.

In another embodiment, the catheter comprises an elongated flexible body having proximal and distal ends and at least one lumen extending therethrough. A tip section comprising a flexible tubing that is more flexible than the catheter body is mounted at the distal end of the catheter body. The flexible tubing has proximal and distal ends and at least on lumen extending therethrough. A tip electrode is mounted on the distal end of the flexible tubing. The tip electrode has an exposed distal region having an outer diameter, a recessed central region having an outer surface proximal to the exposed distal region, and a proximal region having an outer diameter and an outer surface proximal to the central region. The recessed central region has an outer diameter less than the outer diameters of the exposed distal region and the proximal region. The central region and the proximal region are provided with an electrically insulating and thermally conductive layer over at least a portion of their outer surfaces. A ring electrode is mounted on the recessed central region. The ring electrode has an outer diameter less than the outer diameters of the exposed distal region and the proximal region.

DESCRIPTION OF THE DRAWINGS

These and other features and advantages of the present invention will be better understood by reference to the following detailed description when considered in conjunction with the accompanying drawings wherein:

FIG. 3A is a side cross-sectional view of a catheter tip section showing the tip electrode, ring electrode, and lumens for the sensor cable and puller wire.

FIG. 3B is a side cross-sectional view of FIG. 3A showing the tip electrode, ring electrode, and lumens for the sensor cable and thermocouple and electrode lead wires.

DETAILED DESCRIPTION

Figure 1:
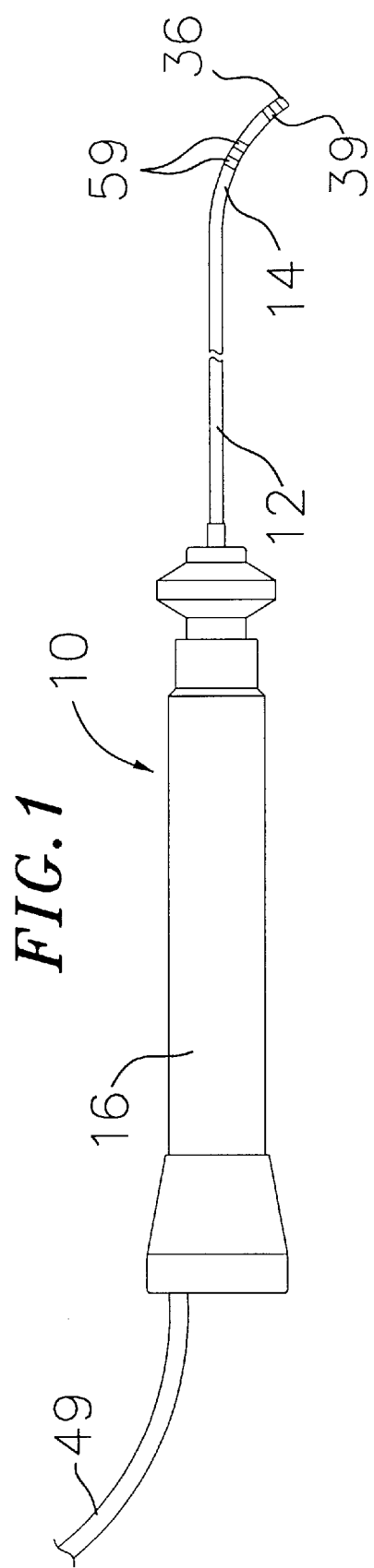
FIG. 1 is a side view of an embodiment of the catheter of the invention.
Figure 2:
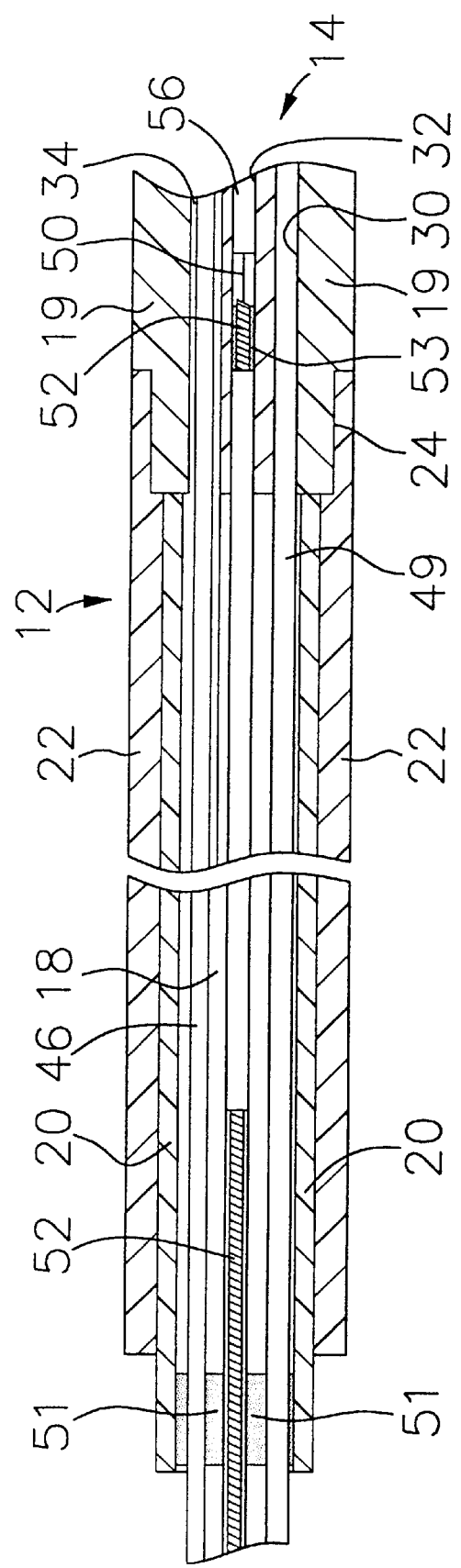
FIG. 2 is a side cross-sectional view of a catheter body according to the invention, including the junction between the catheter body and tip section.

In a particularly preferred embodiment of the invention, there is provided a steerable catheter having two electrodes for making bipolar measurements. As shown in FIGS. 1 and 2, catheter 10 comprises an elongated catheter body 12 having proximal and distal ends, a tip section 14 at the distal end of the catheter body 12, and a control handle 16 at the proximal end of the catheter body 12.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner.

The outer diameter of the catheter body 12 is not critical, but is preferably no more than about 8 french, more preferably about 7 french. Likewise the thickness of the outer wall 22 is not critical, but is thin enough so that the central lumen 18 can accommodate a puller wire, lead wires, and any other wires, cables or tubes. The inner surface of the outer wall 22 is lined with a stiffening tube 20, which can be made of any suitable material, such as polyimide or nylon.

The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness.

One preferred catheter has an outer wall 22 with an outer diameter of from about 0.090 inch to about 0.098 inch and an inner diameter of from about 0.061 inch to about 0.065 inch and a polyimide stiffening tube 20 having an outer diameter of from about 0.060 inch to about 0.064 inch and an inner diameter of from about 0.051 inch to about 0.056 inch. As would be recognized by one skilled in the art, the catheter body construction can be modified as desired. For example, the stiffening tube can be eliminated.

Figure 3C:
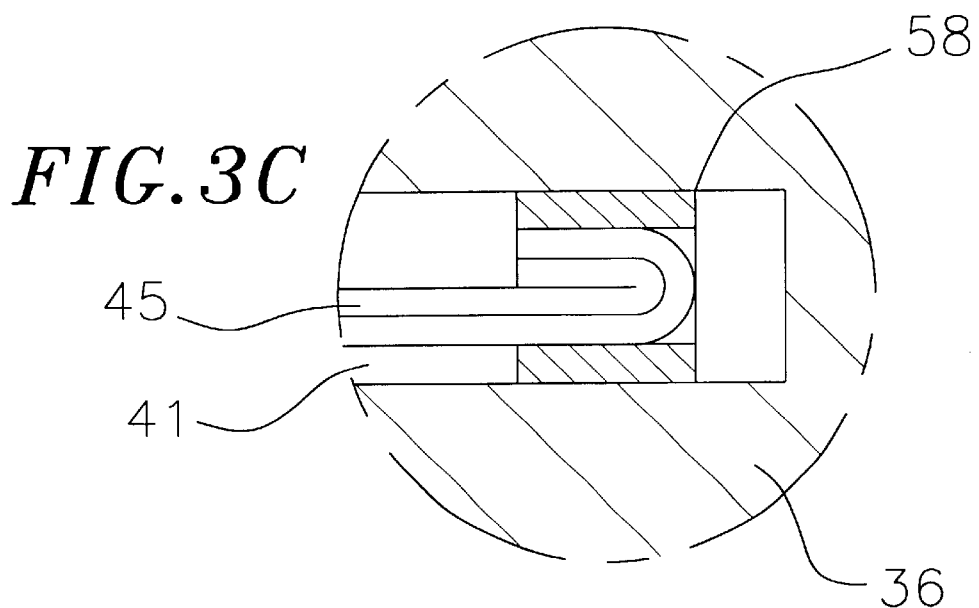
FIG. 3C is an enlarged view of the distal end of the thermocouple mounted in the tip electrode of the catheter of FIGS. 3A and 3B.
Figure 4:
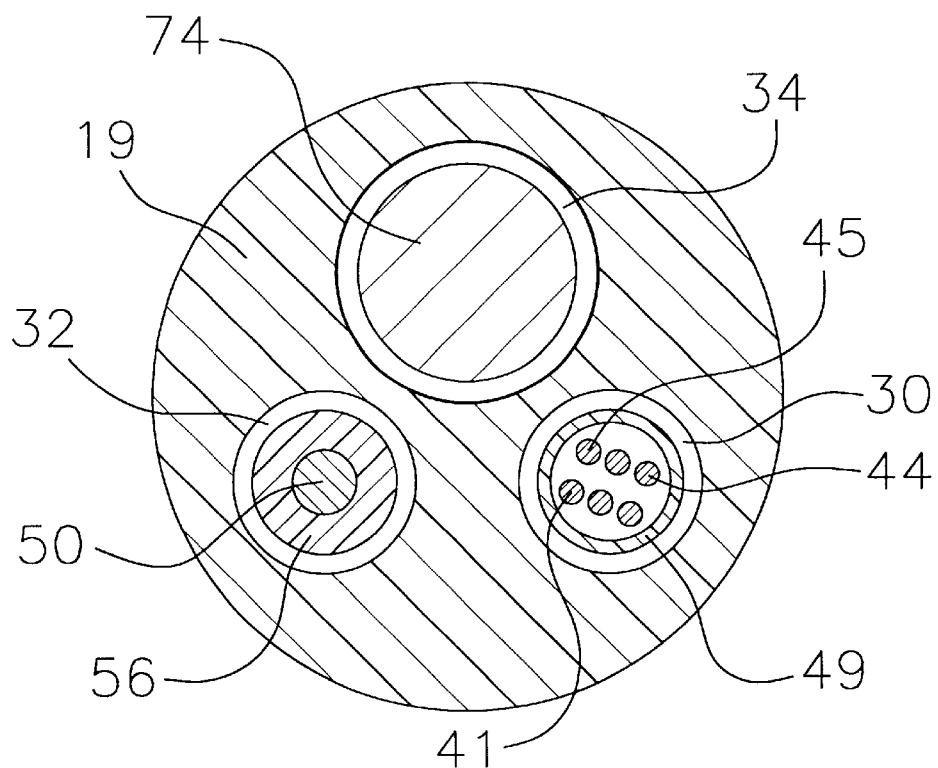
FIG. 4 is a longitudinal cross-sectional view of the tip section illustrated in FIGS. 3A and 3B.

As shown in FIGS. 3A, 3B and 4, the tip section 14 comprises a short section of tubing 19 having three lumens 30, 32 and 34. The tubing 19 is made of a suitable non-toxic material that is preferably more flexible than the catheter body 12. A presently preferred material for the tubing 19 is braided polyurethane, i.e., polyurethane with an embedded mesh of braided high-strength steel, stainless steel or the like. The outer diameter of the tip section 14, like that of the catheter body 12, is preferably no greater than about 8 french, more preferably about 7 french. The size of the lumens is not critical and can vary depending on the specific application. In a particularly preferred embodiment, the tip section 14 has an outer diameter of about 7 french (0.092 inch) and the first lumen 30 and second lumen 32 are generally about the same size, each having a diameter of from about 0.020 inch to about 0.024 inch, preferably 0.022 inch, with the third lumen 34 having a slightly larger diameter of from about 0.032 inch to about 0.038 inch, preferably 0.036 inch.

A preferred means for attaching the catheter body 12 to the tip section 14 is illustrated in FIG. 2. The proximal end of the tip section 14 comprises an outer circumferential notch 24 that receives the inner surface of the outer wall 22 of the catheter body 12. The tip section 14 and catheter body 12 are attached by adhesive (e.g., polyurethane glue) or the like. Before the tip section 14 and catheter body 12 are attached, however, the stiffening tube 20 is inserted into the catheter body 12. The distal end of the stiffening tube 20 is fixedly attached near the distal end of the catheter body 12 by forming a glue joint (not shown) with polyurethane glue or the like. Preferably a small distance, e.g., about 3 mm, is provided between the distal end of the catheter body 12 and the distal end of the stiffening tube 20 to permit room for the catheter body 12 to receive the notch 24 of the tip section 14. A force is applied to the proximal end of the stiffening tube 20, and, while the stiffening tube 20 is under compression, a first glue joint (not shown) is made between the stiffening tube 20 and the outer wall 22 by a fast drying glue, e.g. Super Glue®. Thereafter a second glue joint (not shown) is formed between the proximal ends of the stiffening tube 20 and outer wall 22 using a slower drying but stronger glue, e.g., polyurethane.

At the distal end of the tip section 14 is a tip electrode 36. Preferably the tip electrode 36 generally has a diameter about the same as the outer diameter of the tubing 19. The tip electrode 36 can be made from any suitable material, such as platinum, gold, or stainless steel, and is preferably made of a platinum-iridium alloy (90% platinum/10% iridium).

The tip electrode 36 is generally solid, having first and second blind holes 31 and 33 extending proximally therethrough, as described in more detail below. The tip electrode 36 has a length preferably ranging from about 4 mm to about 14 mm, more preferably from about 6 mm to about 12 mm. As depicted in FIGS. 3A, 3B, 5 and 6, the tip electrode 36 comprises an exposed distal region 35, a proximal region 37, and a recessed central region 38 between the exposed region 35 and the proximal region 37. The exposed region 35 has a length preferably ranging from about 1.5 mm to about 4.0 mm, more preferably from about 2.0 mm to about 3.0 mm, still more preferably from about 2.3 mm to about 2.5 mm, and an outer diameter preferably ranging from about 2.0 mm to about 3.0 mm, more preferably from about 2.3 mm to about 2.5 mm.

In a particularly preferred arrangement, the exposed region has a length similar to its diameter. Preferably the ratio of the length to the diameter ranges from about 0.8:1 to about 1.2:1, more preferably from about 0.9:1 to about 1.1:1. In a particularly preferred embodiment, the length of the exposed region is approximately equal to the diameter of the exposed region. Thus, for example, for a 7 French electrode catheter, the tip electrode preferably has a length and diameter equal to about 2.3 mm. With such a design, the surface area of the tip electrode (having a generally hemispherical distal end) is the same in the parallel orientation and in the perpendicular orientation. These uniform dimensions provide a generally constant contact area between the exposed region 35 of the tip electrode 36 and the heart tissue, irrespective of the orientation of the tip section 14 relative to the heart tissue. As a result, more predictable lesion sizes can be achieved.

The central region 38 is recessed to permit a ring electrode 39 to be mounted thereon with the ring electrode being recessed relative to the exposed region 35 and proximal region 37 to be protected from direct contact with the heart tissue, but permitting contact with surrounding blood, as described in more detail below. Thus, the central portion 38 has an outer diameter that is smaller than the other diameter of the exposed region 35, with the difference between the outer diameter of the central portion and the outer diameter of the exposed region preferably ranging from about 0.1 mm to about 1 mm, more preferably from about 0.5 mm to about 0.7 mm, thus resulting in a recess having a depth ranging from about 0.05 to about 0.4 mm, more preferably about 0.25 mm to about 0.35 mm. The central region 38 preferably has a length slightly greater than the length of the ring electrode 39 mounted thereon. The length of the central region 38 preferably ranges from about 0.5 mm to about 4 mm, more preferably from about 1 mm to about 3 mm.

The proximal region 37 has an outer diameter generally similar to the outer diameter of the exposed region 35. The length of the proximal region 37 preferably ranges from about 3 mm to about 8 mm, more preferably from about 4 mm to about 6 mm.

The tip electrode 36 can be mounted on the distal end of the tubing 19 by any suitable technique. In the depicted embodiment, the proximal end of the proximal region 37 of the tip electrode 36 includes a circumferential notch 26 that mates with a corresponding circumferential notch 27 in the distal end of the tubing 19. The tip electrode 36 is then bonded to the tubing 19 with polyurethane glue or the like. Alternatively, the proximal end of the tip electrode 36 can be provided with a stem, i.e., a region of reduced diameter, that fits into a hole in the distal end of the tubing 19.

The proximal region 37 and central region 38 of the tip electrode 36 are provided with an electrically insulating and thermally conductive layer 55 over at least a portion, and preferably over all, of their outer surfaces. The electrically insulating and thermally conductive layer 55 is made of any suitable electrically insulating and thermally conductive material, including, but not limited to diamond, carbon, parylene, polyimide, polyester, polyurethane, epoxy, ceramic, and combinations thereof. The electrically insulating and thermally conductive layer 55 preferably has a thickness no greater than about 10 μm, more preferably ranging from about 0.5 μm to about 10 μm, still more preferably from about 1 μm to about 5 μm.

The insulating layer 55 can be applied by any suitable technique. For example, a layer of parylene can be applied by a deposition coating technique where the exposed region 35 of the tip electrode 36 is placed in a deposition chamber. The chamber functions to both hold the tip electrode 36 in place, as well as protect the exposed region 35 from exposure to parylene deposits. Alternatively, the insulating layer 55 may comprise a shrink-sleeve made of, for example, a thin polyester (e.g., about 0.00025 inch), or may comprise a thin coating of polyurethane or the like painted onto the surface of the central region 38.

As described above, the ring electrode 39 is mounted on the central portion 38. The ring electrode 39 is fixed in place by glue or the like over the portion of the electrically insulating and thermally conductive layer 55 on the recessed central portion 38. The electrically insulating and thermally conductive layer 55 prevents electrical contact between the ring electrode 39 and the tip electrode 36. The ring electrode 39 can be made of any suitable material, such as platinum, gold, or stainless steel, and is preferably made of a platinum-iridium alloy (90% platinum/10% iridium). The ring electrode 39 is preferably fixed near the distal end of the central portion 38 and in close proximity to the tip portion 35.

The ring electrode can be created by any suitable technique. In one embodiment, the ring electrode 39 comprises a resilient ribbon-shaped conductive material that is wrapped within the recess 26 and fixed in place by glue or the like. The ring electrode 39 can be made of any suitable conductive material, such as those discussed above for the tip electrode. The width and thickness of the ring electrode 39 are suitable for fitting within the recess 26 so that the outer surface of the ring electrode 39 is recessed within the recess 26. In other words, the ring electrode 39 has an outer diameter less than the outer diameter of the exposed region 35. Preferably, the outer diameter of the ring electrode 39 is at least about 5%, more preferably from about 10% to about 20%, less than the outer diameter of the exposed region 35, although the difference between the outer diameters could be greater if desired. The ring electrode 39 has a width preferably ranging from about 0.5 mm to about 4 mm, more preferably from about 1 mm to about 3 mm. In another embodiment, the ring electrode 39 is in the form of a snap ring, where the width and thickness of the ring 39 are suitable for fitting within the recess 26, as described above.

The tip electrode 36 and ring electrode 39 are each connected to a separate lead wire 44. The lead wires 44 extend through the first lumen 30 of tip section 14, the central lumen 18 of the catheter body 12, and the control handle 16, and terminate at their proximal end in an input jack (not shown) that may be plugged into an appropriate signal processing unit and/or source of RF energy (not shown). The portion of the lead wires 44 extending through the central lumen 18 of the catheter body 12, control handle 16 and proximal end of the tip section 14 may be enclosed within a protective sheath 49, which can be made of any suitable material, preferably polyimide (as shown in FIGS. 2 and 4). The protective sheath 49 is preferably anchored at its distal end to the proximal end of the tip section 14 by gluing it in the first lumen 30 with polyurethane glue or the like.

The lead wires 44 are attached to the tip electrode 36 and ring electrodes 39 by any conventional technique. Connection of a lead wire 44 to the tip electrode 36 is accomplished, for example, by soldering the lead wire 44 into the second blind hole 33.

Figure 5:
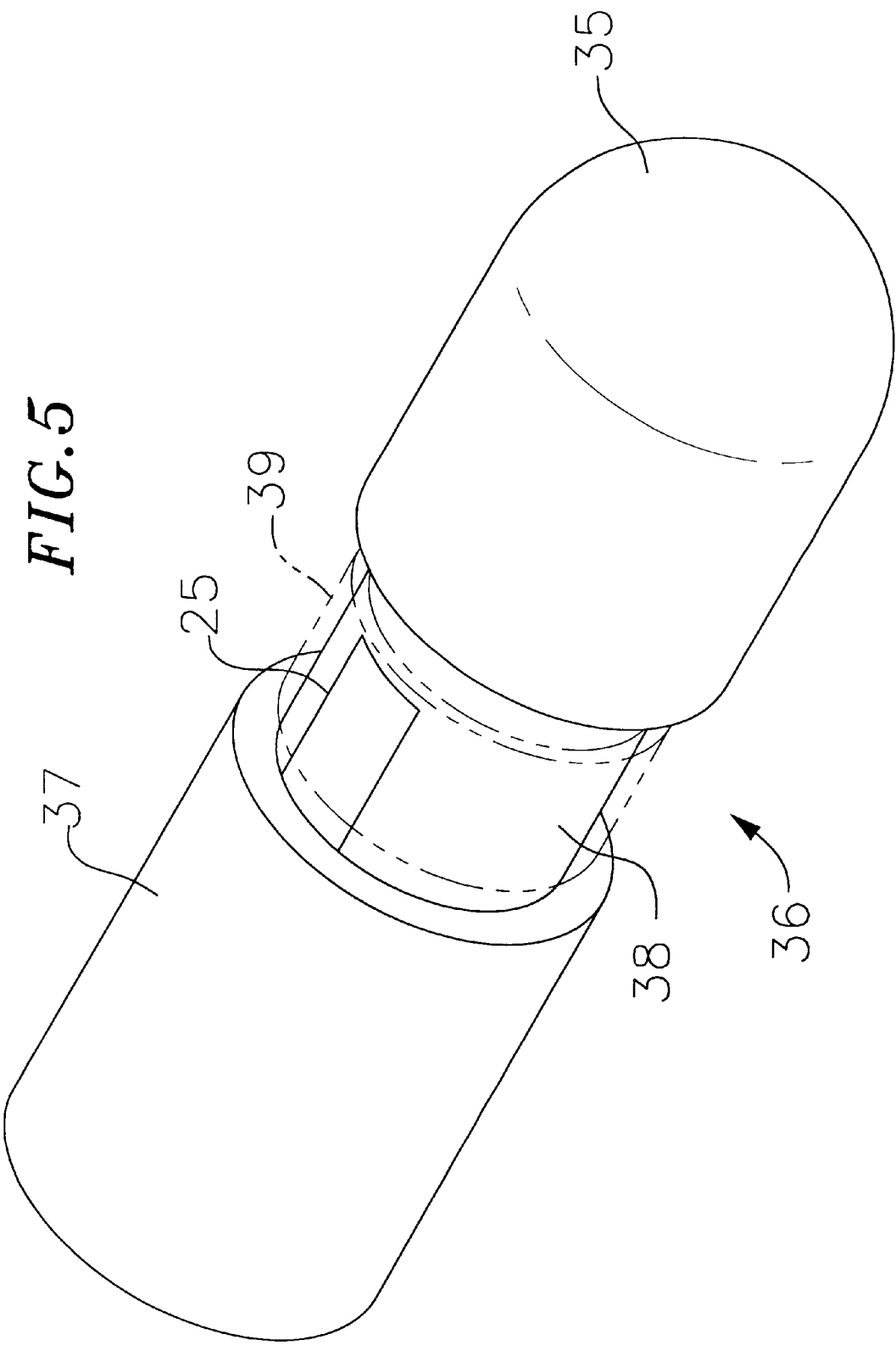
FIG. 5 is a perspective view of the tip electrode depicted in FIGS. 3A and 3B.
Figure 6:
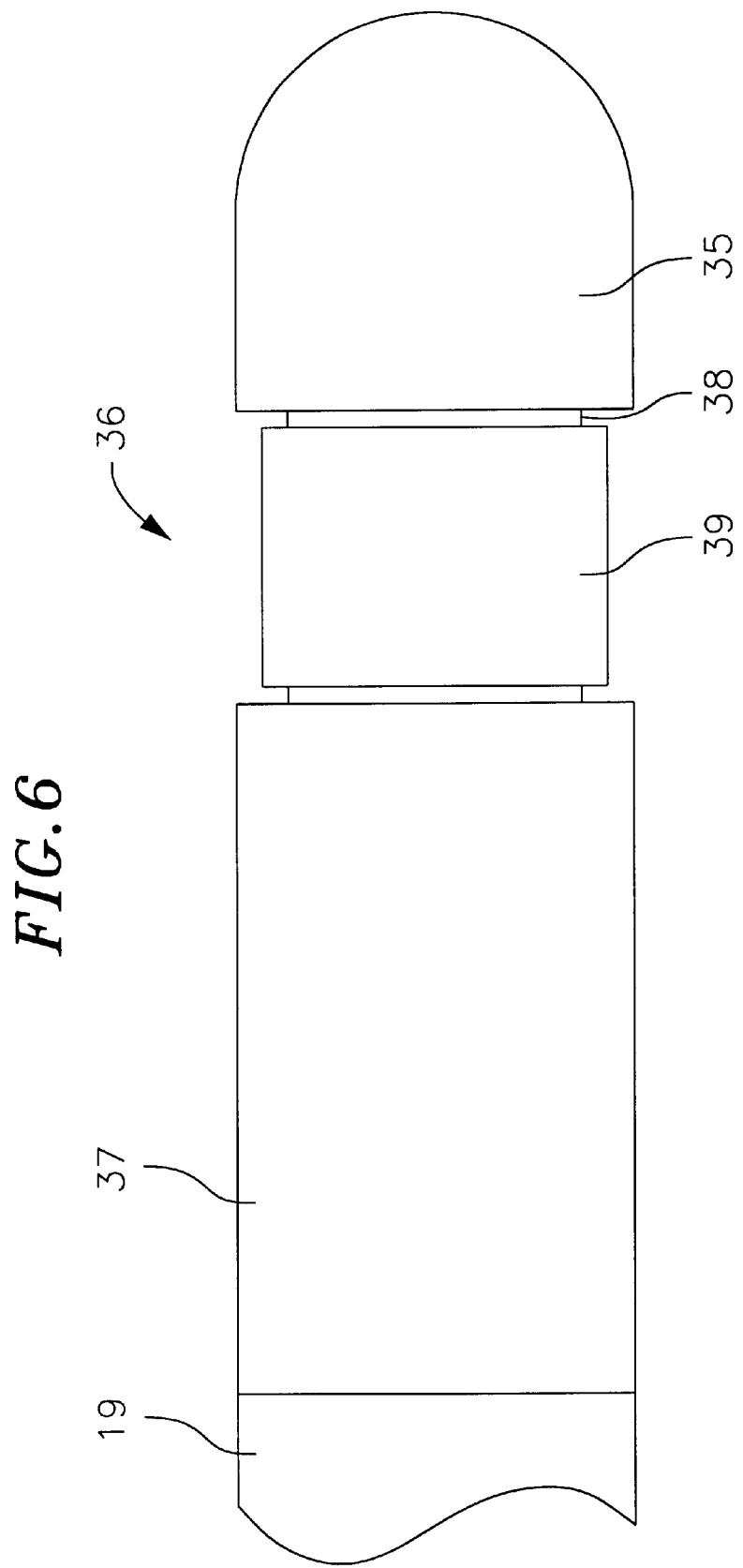
FIG. 6 is a side view of the tip electrode depicted in FIGSs. 3A and 3B.

The lead wire 44 for the ring electrode 39 extends through the first blind hole 31 in the tip electrode 36 and through an opening 25 in the side of the ring electrode, as shown in FIGS. 3A and 5. The ends of the lead wire 44 are then stripped of any coating and soldered or welded to the underside of the ring electrode 39, which is positioned over the opening 25 and fixed in place with polyurethane glue or the like. Once the ring electrode 39 is fixed in place, extra polyurethane glue 28 is used to seal the region between the distal end of the proximal region 37 and the ring electrode in the general area of the opening 25 to protect internal components of the catheter from surrounding fluids.

Two additional ring electrodes 59 are mounted of the distal end the tip section 14. The ring electrodes 59 are slid over the flexible tubing 19 and fixed in place by glue of the like. The position and. spacing of the additional ring electrode 59 are not critical. If desired, more or less ring electrodes 59 may be used and can be positioned over the flexible tubing 19 of the tip section 14.

A temperature sensing means is provided for the tip electrode 36 and, if desired, one or more of the ring electrodes 39 and 59. Any conventional temperature sensing means, e.g., a thermocouple or thermistor, may be used. A preferred temperature sensing means for the tip electrode 36 comprises a thermocouple formed by an enameled wire pair. One wire of the wire pair is a copper wire 41, e.g., a number 40 copper wire. The other wire of the wire pair is a constantan wire 45. The wires 41 and 45 of the wire pair are electrically isolated from each other except at their distal ends where they are twisted together, covered with a short piece of plastic tubing 58, e.g., polyamide, and covered with epoxy (as shown in FIG. 3c). The plastic tubing 58 is then attached in the distal end of the first blind hole 31 of the tip electrode 36 by polyurethane glue or the like. Alternatively, the wires 41 and 45 can be soldered in the blind hole 31. The distal end of the first blind hole 31 preferably has a smaller diameter than the proximal end (which is sized to accommodate a location sensor, as described further below). The distal end of the blind hole 31 preferably has a size suitable for fitting the tubing 58 and wires 41 and 45 snugly into the blind hole. The distal end of the blind hole 31 is preferably positioned in the middle of the exposed region 35 to provide accurate temperature measurement by the thermocouple wires 41 and 45 mounted therein.

The wires 41 and 45 extend through the second lumen 32 in the tip section 14 and through the central lumen 18 of the catheter body 12. The wires 41 and 45 then extend out through the control handle 16 and to a connector (not shown) connectable to a temperature monitor (not shown).

Alternatively, the temperature sensing means may be a thermistor. A suitable thermistor for use in the present invention is Model No. AB6N2-GC 14KA143E/37C sold by Thermometrics (New Jersey).

Additionally, a location sensor 72, preferably an electromagnetic location sensor, is contained within the distal end of the tip section 14. The electromagnetic location sensor 72 is located within the proximal end of the first blind hole 31 in the tip electrode 36 and fixed by polyurethane glue or the like. The electromagnetic sensor 72 is connected to an electromagnetic sensor cable 74, which extends through the third lumen 34 of the tip section 14, through the catheter body 12, and out through control handle 16. The electromagnetic sensor cable 74 comprises multiple wires encased within a plastic covered sheath. The sensor cable 74 is connected to a circuit board, which amplifies the signal received from the electromagnetic sensor 72 and transmits it to a computer in a form understandable by the computer. In a particularly preferred embodiment, the circuit board is contained within the control handle 16, as described in U.S. patent application Ser. No. 08/924,616, entitled "Steerable Direct Myocardial Revascularization Catheter", the disclosure of which is incorporated herein by reference. Suitable electromagnetic sensors for use with the present invention are described, for example, in U.S. patent application Ser. No. 09/160,063 (entitled "Miniaturized Position Sensor") and U.S. Pat. Nos. 5,558,091, 5,443,489, 5,480,422, 5,546,951, 5,568,809, and 5,391,199 and International Publication No. WO 95/02995, the disclosures of which are incorporated herein by reference. If desired, the sensor 72 can alternatively be contained, at least in part, within a rigid plastic housing, e.g., made of polyetheretherketone (PEEK), that is mounted between the tip electrode 36 and the flexible tubing 19. Such a design is described in U.S. Pat. No. 5,938,603, the disclosure of which is incorporated herein by reference.

Additionally, a mechanism is provided for deflecting the tip section 14. In one embodiment, the mechanism comprises a puller wire 50 extending through the catheter body 12. The puller wire 50 is anchored at its proximal end to the control handle 16 and is anchored at its distal end to the tip section 14. The puller wire 50 is made of any suitable metal, such as stainless steel or Nitinol, and is preferably coated with Teflon® or the like. The coating imparts lubricity to the puller wire 50. The puller wire 50 preferably has a diameter ranging from about 0.006 to about 0.010 inches.

A compression coil 52 is situated within the catheter body 12 in surrounding relation to the puller wire 50. The compression coil 52 extends from the proximal end of the catheter body 12 to the proximal end of the tip section 14. The compression coil 52 is made of any suitable metal, preferably stainless steel. The compression coil 52 is tightly wound on itself to provide flexibility, i.e., bending, but to resist compression. The inner diameter of the compression coil 52 is preferably slightly larger than the diameter of the puller wire 50. The Teflon® coating on the puller wire 50 allows it to slide freely within the compression coil 52. If desired, particularly if the lead wires 44 are not enclosed by a protective sheath 49, the outer surface of the compression coil 52 can be covered by a flexible, non-conductive sheath 46, e.g., made of polyimide tubing, to prevent contact between the compression coil 52 and any other wires within the catheter body 12.

The compression coil 52 is anchored at its proximal end to the proximal end of the stiffening tube 20 in the catheter body 12 by glue joint 51 and at its distal end to the tip section 14 by glue joint 53. Both glue joints 51 and 53 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 52 and wicks around the outer circumference to form a glue joint about the entire circumference of the compression coil 52.

The puller wire 50 extends into the second lumen 32 of the tip section 14. The puller wire 50 is anchored at its distal end to the tip electrode 36 within the second blind hole 33 along with the lead wire 44. A preferred method for anchoring the puller wire 50 within the tip electrode 36 is by crimping metal tubing 54 to the distal end of the puller wire 50 and soldering the metal tubing 54 inside the second blind hole 33. Anchoring the puller wire 50 within the tip electrode 36 provides additional support for the tip electrode 36 on the flexible plastic tubing 19, reducing the likelihood that the tip electrode 36 will separate from the tubing 19. Alternatively, the puller wire 50 can be attached to the side of the tip section 14. Such a design is described in U.S. patent application Ser. No. 08/924,611 (filed Sep. 5, 1997), the disclosure of which is incorporated herein by reference. Within the second lumen 32 of the tip section 14, the puller wire 50 extends through a plastic, preferably Teflon®, sheath 56, which prevents the puller wire 50 from cutting into the wall of the tubing 19 when the tip section is deflected.

Longitudinal movement of the puller wire 50 relative to the catheter body 12, which results in deflection of the tip section 14, is accomplished by suitable manipulation of the control handle 16. A suitable control handle design for use with the present invention is described in U.S. patent application Ser. No. 08/982,113, filed Dec. 1, 1997, the disclosure of which is incorporated herein by reference. If desired, the catheter can be multidirectional, i.e., having two or more puller wires to enhance the ability to manipulate the tip section in more than one direction or to form two or more different curves. A description of such a design is provided in U.S. patent application Ser. Nos. 08/924,611 (filed Sep. 5, 1997), Ser. No. 09/130,359 (filed Aug. 7, 1998), Ser. No. 09/143,426 (filed Aug. 28, 1998), Ser. No. 09/205,631 (filed Dec. 3, 1998), and Ser. No. 09/274,050 (filed Mar. 22, 1999), the disclosures of which is incorporated herein by reference.

The catheters in accordance with the present invention are particularly suitable for mapping the heart and ablating heart tissue, such as accessory signal pathways causing arrhythmias. In operation, the distal end of the catheter 10 is inserted into a vein or artery and advanced into the heart. To assist in positioning the tip section 14 of the catheter 10 at a desired position within the heart, the puller wire 50 and control handle 16 are used to deflect the tip section 14. Once the tip section 14 has been positioned at or near the desired location of the heart tissue, the electrical activity of the heart may be identified, evaluated or mapped, and electrophysiological sources of arrhythmia may be identified and/or treated.

More specifically the bipolar electrode pair, namely, the exposed region 35 of the tip electrode 36 and ring electrode 39 mounted on the tip electrode, is used to map the electrical activity of the heart. The catheter of the present invention is designed such that the exposed region 35 of the tip electrode 36 is in direct contact with the heart tissue. Thus, the exposed region 35 senses both the local activation energy (near-field signals) at the point of contact with the heart tissue and far field activation energy (far-field signals) received by the exposed region through the blood. However, the ring electrode 39 is recessed relative to the exposed region 35 to be protected from direct contact with the heart tissue, but permitting contact with surrounding blood. The close proximity of the ring electrode 39 to the exposed region 35 enables the ring electrode to receive approximately the same far-field signals as the exposed region.

However, the ring electrode 39 does not pick up the local activation potential (near-field signals) that are received by the exposed region 35. The signals received by the exposed region 35 and the ring electrode 39 are sent to a suitable signal processing unit. Within the signal processing unit, the signal detected by the ring electrode 39, which includes only far-field activity, is subtracted from the signal detected by the exposed region 35 of the tip electrode 36, which includes both near-field and far-field activity. Thus, the near-field signals can be more accurately determined. This improved method of detecting electrical activity allows the physician or operator to determine the location of the arrhythmiogenic focus more accurately for ablating and other purposes.

Additionally, the electrically insulating layer 55 limits the electrically active surface area of the tip electrode 36 to the exposed region 35, providing improved electrogram resolution compared to a conventional tip electrode. More specifically, electrograms recorded from the relatively small exposed region 35 will be more discrete, reporting electrical activity from a smaller area of tissue.

The electromagnetic location sensor 72 in the tip section 14 of the catheter is used to provide a map of the heart so that the physician can better determine where to ablate and can have a better sense for where the tip section 14 is located during the procedure. In use, the patient is placed in a magnetic field generated, for example, by situating under the patient a pad containing coils for generating a magnetic field, and a reference electromagnetic sensor is fixed relative to the patient, e.g., taped to the patient's back. Signals generated in the heart by both the fixed reference sensor and the electromagnetic location sensor 72 in the catheter are amplified and transmitted to a computer that analyzes the signals and displays them on a monitor. By this method, the precise location of the location sensor 72 (and thus the tip section 14, including the tip electrode 36) relative to the reference sensor can be ascertained and visually displayed. The sensor 72 can also detect displacement of the catheter that is caused by contraction of the heart muscle.

The electromagnetic mapping sensor 72 preferably is used in combination with the tip electrode 36 and ring electrodes 39. By combining the electromagnetic sensor 72 and electrodes 36 and 39, a physician can simultaneously map the contours or shape of the heart chamber, the electrical activity of the heart, and the extent of displacement of the catheter. The tip electrode 36 and ring electrode 38 are used to monitor the strength of the electrical signals at a particular location. As would be recognized by one skilled in the art, the inventive tip electrode design can be effectively used without the inclusion of a location sensor, and thus the electromagnetic sensor 72 can be eliminated if desired.

Once the electrical activity of the heart is determined and mapped, if desired, the physician uses the same catheter for ablating the heart tissue. The relatively large surface area of the tip electrode 36, which includes the exposed region 35 as well as the proximal region 37 and central region 38, which are covered with the thermally conductive layer 55, enhances the ability of the electrode to dissipate heat during ablation compared to a comparable tip electrode having a length closer to the that of the exposed region 35 of the present catheter. Compared to a standard 4 mm tip electrode, the tip electrode of the present invention having a preferred length of about 6 mm to about 8 mm provides improved convective cooling by the passing blood, such that additional power can be applied to the tissue. However, conventional 8 mm tip electrodes require more power than the inventive tip electrode. The tip electrode of the present invention preferably has an exposed length of only about 2 mm to about 3 mm, reducing the amount of power required to ablate compared to a tip electrode have an exposed length of 8 mm. Further, a conventional 8 mm tip electrode uses more energy heating the surrounding blood rather than heating the adjacent heart tissue. This heating of the blood can cause significant coagulation of the blood along the surface of the tip electrode. The present invention overcomes this problem by providing an electrically insulating, but thermally conductive layer over the non-exposed portion of the tip electrode 36, allowing the electrical power to be concentrated at the exposed region 35, while the insulated portion (the central region 38) of the tip electrode is convectively cooled by passing blood.

As a result of this design, more power can be applied to the tissue with the inventive electrode compared to a standard tip electrode having a total length equal to the length of the exposed region 35 of the inventive electrode. This holds true because the blood can more efficiently cool the inventive electrode compared to the standard tip electrode. Additionally, the inventive electrode can create the same sized lesion as a standard tip electrode having a total length equal to the total length of the inventive electrode (but without an electrically insulating and thermally conductive covering), but using less power. This holds true because the inventive electrode has a higher current density than a standard tip electrode, while still having similar cooling capabilities, and therefore less power is needed.

Additionally, as discussed above, electrode impedance is routinely monitored during ablation to detect the potential formation of dangerous char or thrombus on the tip electrode. Because the electrically active area (i.e., the exposed region 35) of the inventive tip electrode is smaller than with conventional ablation tip electrodes that offer similar cooling ability, changes in impedance due to char or thrombus formation are more readily detected with the inventive catheter.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
    an elongated flexible body having a distal region and at least one lumen extending therethrough;
    a tip electrode mounted on the distal region, the tip electrode having an exposed distal region having an outer diameter, a recessed central region having an outer surface proximal to the exposed distal region, and a proximal region having an outer diameter and an outer surface proximal to the central region, wherein the recessed central region has an outer diameter less than the outer diameters of the exposed distal region and the proximal region, and further wherein the central region and the proximal region are provided with an electrically insulating and thermally conductive layer over at least a portion of their outer surfaces; and
    a ring electrode mounted on the recessed central region and having an outer diameter less than the outer diameters of the exposed distal region and the proximal region.

2. A catheter as claimed in claim 1, wherein the tip electrode has a length ranging from about 4 mm to about 12 mm.

3. A catheter as claimed in claim 1, wherein the tip electrode has a length ranging from about 6 mm to about 10 mm.

4. A catheter as claimed in claim 1, wherein the exposed distal region has a length ranging from about 1.5 mm to about 4.0 mm.

5. A catheter as claimed in claim 1, wherein the exposed distal region has a length ranging from about 2 mm to about 3 mm.

6. A catheter as claimed in claim 1, wherein the exposed region has a length approximately equal to its outer diameter.

7. A catheter as claimed in claim 1, wherein the difference between the outer diameter of the central portion and the outer diameter of the exposed region ranges from about 0.25 mm to about 1.5 mm.

8. A catheter as claimed in claim 1, wherein the difference between the outer diameter of the central portion and the outer diameter of the exposed region ranges from about 0.5 mm to about 1 mm.

9. A catheter as claimed in claim 1, wherein the electrically insulating and thermally conductive layer comprises a composition selected from the group consisting of diamond, carbon, parylene, polyimide, polyester, polyurethane, epoxy, ceramic, and combinations thereof.

10. A catheter as claimed in claim 1, wherein the electrically insulating and thermally conductive layer has a thickness no greater than about 10 μm.

11. A catheter as claimed in claim 1, wherein the electrically insulating and thermally conductive layer has a thickness ranging from about 1 μm to about 5 μm.

12. A catheter comprising:
   an elongated flexible body having proximal and distal ends and at least one lumen extending therethrough;
   a tip section comprising a flexible tubing that is more flexible than the catheter body mounted at the distal end of the catheter body, the flexible tubing having proximal and distal ends and at least on lumen extending therethrough;
   a tip electrode mounted on the distal end of the flexible tubing, the tip electrode having an exposed distal region having an outer diameter, a recessed central region having an outer surface proximal to the exposed distal region, and a proximal region having an outer diameter and an outer surface proximal to the central region, wherein the recessed central region has an outer diameter less than the outer diameters of the exposed distal region and the proximal region, and further wherein the central region and the proximal region are provided with an electrically insulating and thermally conductive layer over at least a portion of their outer surfaces; and
   a ring electrode mounted on the recessed central region and having an outer diameter less than the outer diameters of the exposed distal region and the proximal region.

13. A catheter as claimed in claim 12, wherein the tip electrode has a length ranging from about 4 mm to about 12 mm.

14. A catheter as claimed in claim 12, wherein the tip electrode has a length ranging from about 6 mm to about 10 mm.

15. A catheter as claimed in claim 12, wherein the electrically insulating and thermally conductive layer comprises a composition selected from the group consisting of diamond, carbine, polyimide, polyester, polyurethane, epoxy, ceramic, and combinations thereof.

16. A catheter as claimed in claim 12, wherein the electrically insulating and thermally conductive layer has a thickness no greater than about 10 μm.

17. A catheter as claimed in claim 12, wherein the electrically insulating and thermally conductive layer has a thickness ranging from about 1 μm to about 5 μm.

18. A catheter as claimed in claim 12, wherein the exposed region has a length approximately equal to its outer diameter.

19. A catheter as claimed in claim 12, wherein the exposed distal region has a length ranging from about 1.5 mm to about 4.0 mm.

20. A catheter as claimed in claim 12, wherein the exposed distal region has a length ranging from about 2 mm to about 3 mm.

21. A catheter as claimed in claim 12, wherein the difference between the outer diameter of the central portion and the outer diameter of the exposed region ranges from about 0.25 mm to about 1.5 mm.

22. A catheter as claimed in claim 12, wherein the difference between the outer diameter of the central portion and the outer diameter of the exposed region ranges from about 0.5 mm to about 1 mm.

23. A catheter as claimed in claim 12, further comprising at least one ring electrode mounted on the distal end of the flexible tubing.

24. A catheter as claimed in claim 12, further comprising means for deflecting the tip section.

25. A catheter as claimed in claim 12, further comprising a location sensor mounted, at least in part, in the tip electrode.

* * * * *